US007892211B2

(12) United States Patent
McCulloch et al.

(10) Patent No.: US 7,892,211 B2
(45) Date of Patent: Feb. 22, 2011

(54) CLOSURE CONTAINER FOR SINGLE DOSE DISPOSABLE PHARMACEUTICAL DELIVERY SYSTEM

(75) Inventors: James Stanley McCulloch, St. Peters, MO (US); Steven Dale Kelly, St. Peters, MO (US)

(73) Assignee: Seratouch, L.L.C., St. Peters, MO (US)

( * ) Notice: Subject to any disclaimer, the term of this patent is extended or adjusted under 35 U.S.C. 154(b) by 0 days.

(21) Appl. No.: 12/425,705

(22) Filed: Apr. 17, 2009

(65) Prior Publication Data

US 2009/0247954 A1 Oct. 1, 2009

Related U.S. Application Data

(63) Continuation of application No. 11/456,452, filed on Jul. 10, 2006, now abandoned.

(60) Provisional application No. 60/746,261, filed on May 3, 2006.

(51) Int. Cl.
*A61M 5/00* (2006.01)
(52) U.S. Cl. .................. 604/192; 604/187; 604/189; 604/200; 604/212
(58) Field of Classification Search .............. 604/187, 604/198, 192, 200, 212
See application file for complete search history.

(56) References Cited

U.S. PATENT DOCUMENTS

| 2,618,263 | A |   | 11/1952 | Lakso et al. |         |
|-----------|---|---|---------|--------------|---------|
| 2,676,591 | A |   | 4/1954  | Fox et al.   |         |
| 2,680,440 | A |   | 6/1954  | Fox et al.   |         |
| 2,687,727 | A |   | 8/1954  | Lawshe       |         |
| 2,693,183 | A |   | 11/1954 | Lockhart     |         |
| 2,771,879 | A |   | 11/1956 | Salisbury, Jr. |       |
| 2,876,771 | A | * | 3/1959  | Dunmire      | 604/141 |
| 2,895,475 | A | * | 7/1959  | Cole         | 600/578 |
| 3,192,925 | A |   | 7/1965  | Cunningham   |         |
| 3,736,933 | A |   | 6/1973  | Szabo        |         |
| 4,013,073 | A |   | 3/1977  | Cunningham   |         |
| 4,022,206 | A |   | 5/1977  | Hilleman et al. |      |
| 4,093,067 | A | * | 6/1978  | Hollander, Jr. | 426/109 |
| 4,130,117 | A | * | 12/1978 | Van Eck      | 604/200 |
| 4,227,611 | A | * | 10/1980 | Hollander, Jr. | 206/219 |

(Continued)

OTHER PUBLICATIONS

Owen Mumford Ltd; "Snapdragon-Single-Use Disposable Auto Injector" webpage: pharmaceutical-technology.com; Jun. 21, 2006; 3 pages.

*Primary Examiner*—Nicholas D Lucchesi
*Assistant Examiner*—Aarti B Berdichevsky
(74) *Attorney, Agent, or Firm*—SNR Denton US L.L.P.

(57) ABSTRACT

The disposable unit dose pharmaceutical delivery system may be used by trained medical personnel for intradermal or subcutaneous injections in applications currently being serviced by conventional pre-filled syringes. The delivery system may also be used by personnel with little or no medical training for mass immunizations in underdeveloped parts of the world, insulin injections, and/or emergency epinephrine injections. The delivery system includes an envelope with a tear-away section and a dispensing section. When the tear-away section has been removed, a needle is exposed and is ready for insertion in the patient. The dispensing portion is squeezed between the thumb and forefinger to inject the pharmaceutical into the patient. The exterior surface of the envelope may be used for advertising by a pharmaceutical producer, a supplier or otherwise.

17 Claims, 3 Drawing Sheets

U.S. PATENT DOCUMENTS

| | | |
|---|---|---|
| 4,282,986 A | 8/1981 | Ekenstam et al. |
| 4,548,601 A | 10/1985 | Lary |
| 4,692,157 A | 9/1987 | Landau et al. |
| 4,772,271 A | 9/1988 | Meyer et al. |
| 4,883,473 A | 11/1989 | Thomas |
| 4,935,011 A | 6/1990 | Hogan |
| 4,955,871 A | 9/1990 | Thomas |
| 5,019,048 A | 5/1991 | Margolin |
| 5,261,881 A | 11/1993 | Riner |
| 5,370,626 A | 12/1994 | Farris |
| 5,509,906 A | 4/1996 | Poynter |
| 5,538,506 A | 7/1996 | Farris et al. |
| 5,810,783 A | 9/1998 | Claro et al. |
| 5,873,860 A | 2/1999 | Kahlert et al. |
| 6,120,478 A | 9/2000 | Moore et al. |
| 6,585,693 B1 | 7/2003 | Dischler |
| 6,605,064 B2 | 8/2003 | Hatch |
| 7,247,151 B2 | 7/2007 | Slawson |
| 2005/0215955 A1 | 9/2005 | Slawson |

* cited by examiner

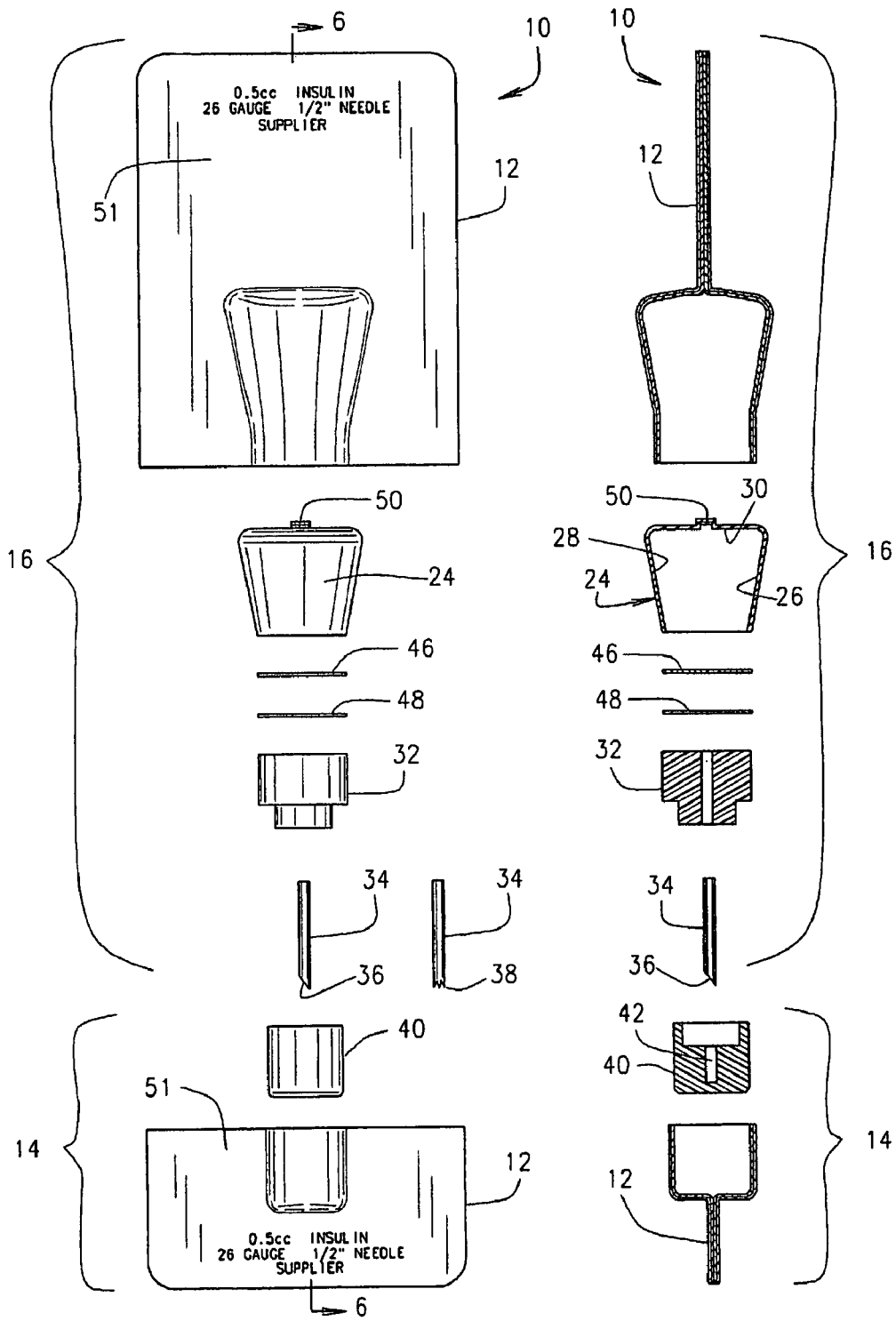

CLOSURE CONTAINER FOR SINGLE DOSE DISPOSABLE PHARMACEUTICAL DELIVERY SYSTEM

CROSS-REFERENCE TO RELATED APPLICATIONS

This application is a Continuing Application of U.S. application Ser. No. 11/456,452, filed Jul. 10, 2006, which claims priority to U.S. Provisional Application Ser. No. 60/746,261, filed on May 3, 2006, each of which are incorporated herein by reference in their entirety.

BACKGROUND

This invention relates to closure containers for single dose disposable pharmaceutical delivery systems. The system has particular advantage for battlefield applications, mass immunizations in underdeveloped areas of the world and other general medical applications currently being serviced by prefilled syringes.

During World War II Squibb, now Bristol-Myers Squibb, developed the disposable morphine Syrette®. It consisted of a small tube of morphine with an attached hypodermic needle. Medical personnel first had to break a seal with a small needle. The morphine was administered by piercing the patient's skin with the needle and then squeezing the tube.

A number of prior art patents for a disposable single dose dispenser utilize a moveable needle to puncture the container holding the pharmaceutical including U.S. Pat. Nos. 2,676,591; 2,687,727; 2,693,183; 3,192,925 and 4,883,473. The present invention does not utilize a moveable needle to puncture the container holding the pharmaceutical.

U.S. Pat. No. 2,618,263 for a "Disposable Single-Use Syringe" is a disposable, single use, prefilled unit dose pharmaceutical delivery system; however, the structural design is different from the present invention. In the '263 Patent, the ampoule is easily moved by a finger so that the needle punctures the ampoule, whereupon with further pressure being exerted on the ampoule, the contents thereof is expressed through the needle for the intended function of the syringe. The needle in the present invention is straight and the needle in the '263 Patent is not.

U.S. Pat. No. 3,736,933 is a "Burstable Seamed Hypodermic Applicator." This prior art patent does not show a single dispensing apparatus with a single cap. Rather, the '933 Patent discloses a plurality of dispensing applicators in a single elongate shield to receive and cap multiple needles. In other words, this patent discloses a package with several dispensing applicators that can be selectively withdrawn from the single elongate shield/cap. The present invention uses a single shield/cap for each dispensing apparatus.

U.S. Pat. No. 4,548,601 is a "Prepackaged, Injectable Pharmaceutical and Hypodermic Needle Combination." The combination is a disposable, single use, prefilled unit dose pharmaceutical delivery system; however, the structural design is different from the present invention. In the '601 Patent, "the injectable medication is contained within a substantially non-resilient, highly flexible sack or inner container which is indirectly compressed, pneumatically, by means of a resilient, comparatively rigid outer container. Manual collapsing pressure or squeezing of the outer container serves, in successive operations, to completely discharge the contents of the inner container through a cannulae, thereby injecting its full dose." The present invention does not use the pneumatic pump of this prior art patent; instead, the present invention relies on manual pressure of the thumb and forefinger to discharge the pharmaceutical from the bladder. This prior art patent discloses a rupture seal, but no fill port.

U.S. Pat. No. 4,955,871 is a "Single-Use Disposable Syrette" that is prefilled unit dose pharmaceutical delivery system; however, the structural design is different from the present invention. The '871 Patent is designed to allow aspiration for intramuscular and intravenous injections whereas the present invention is not designed for aspiration. The '871 Patent is designed to create negative pressure in a reservoir means 46 formed from a pair of sheets 38a and 38b. The bladder of the present invention is not designed to create negative pressure. The present invention uses a needle seal that is ruptured by pressure. The '871 Patent uses the sharp end of the needle to penetrate the nozzle membrane 22. The '871 Patent discloses a fill port 58 for the reservoir 46, but no rupture seal.

U.S. Pat. No. 5,019,048 is a "Unit Dose Syringe with Rotatable Needle." This prior art patent discloses a disposable, single use, prefilled unit dose pharmaceutical delivery system; however, the structural design is different from the present invention. FIGS. 7 and 8 show an embodiment wherein a needle 55 is connected to a plastic squeeze bag 56 by an unstructured flexible plastic fitting at 57 in the manner of a bagpipe where the needle is analogous to the pipe of the bagpipe. FIG. 7 shows the needle 55 in the protected position inside a pocket 59. Pocket 59 includes a tear strip, not shown, which is removed to allow needle 55 to assume the position shown in FIG. 8. In use, a chuck 60 grips the needle as shown in FIG. 9. Once the needle is secured in the chuck, the contents of the bag are easily administered. Unlike this prior art patent, the present invention does not have a separate chuck for administration of the pharmaceutical, nor does the present invention have a rotating needle.

U.S. Pat. No. 5,810,783 is a "Medication Injector" which is a disposable, single use, prefilled unit dose pharmaceutical delivery system; however, the structural design is different from the present invention. To avoid fluid escape during storage, from this prior art patent, the needle 4 is enclosed in a flexible plastic tube 5, closed at its distal end 6 by heat-sealing, to keep air inside the needle 4, acting as a blockage to the fluid. The tube 5 is further enclosed in an air tight envelope 7 as best seen in FIGS. 1A and 2 of this prior art patent. The present invention uses a single cap to shield the needle, unlike this two part shielding system in the '783 Patent.

Owen Mumford Ltd. of Oxon in the United Kingdom advertises a "Snapdragon" single use disposable auto injector. The device is promoted as a single-use, disposable, safety injection device for use with a pre-filled glass syringe. The present invention does not use a pre-filled glass syringe.

Many attempts have been made to produce a single dose disposable pharmaceutical delivery system to replace conventional prefilled syringes; unfortunately none of these attempts have been economically competitive. There remains a need for a reliable unit dose disposable pharmaceutical delivery system that is economical to produce.

SUMMARY OF THE INVENTION

The unit dose disposable pharmaceutical delivery system is formed as a generally flat envelope about the size of a credit card having a tear-away portion and a dispensing portion. The pharmaceutical is stored in a bladder and is dispensed through a needle that is stationary in relationship to the bladder. In other words, the needle is not moved to puncture the bladder, prior to dispensing of the pharmaceutical. This delivery system is used to make intradermal or subcutaneous injections and thus the exposed portion of the needle can be relatively short. This system has particular advantage for battlefield applications, mass immunizations in underdeveloped areas of the world, and other general medical applications currently being serviced by pre-filled syringes. The delivery system may also be helpful to numerous individuals that do not have formal medical training, such as for insulin injections and/or emergency epinephrine injections.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

FIG. 5 is a top plan view of the exploded components of the unit dose disposable pharmaceutical delivery system; and FIG. 6 is a section view of the exploded components of the unit dose disposable pharmaceutical delivery system of FIG. 6 along the line 7-7.

DETAILED DESCRIPTION OF THE INVENTION

Figures 1, 2:
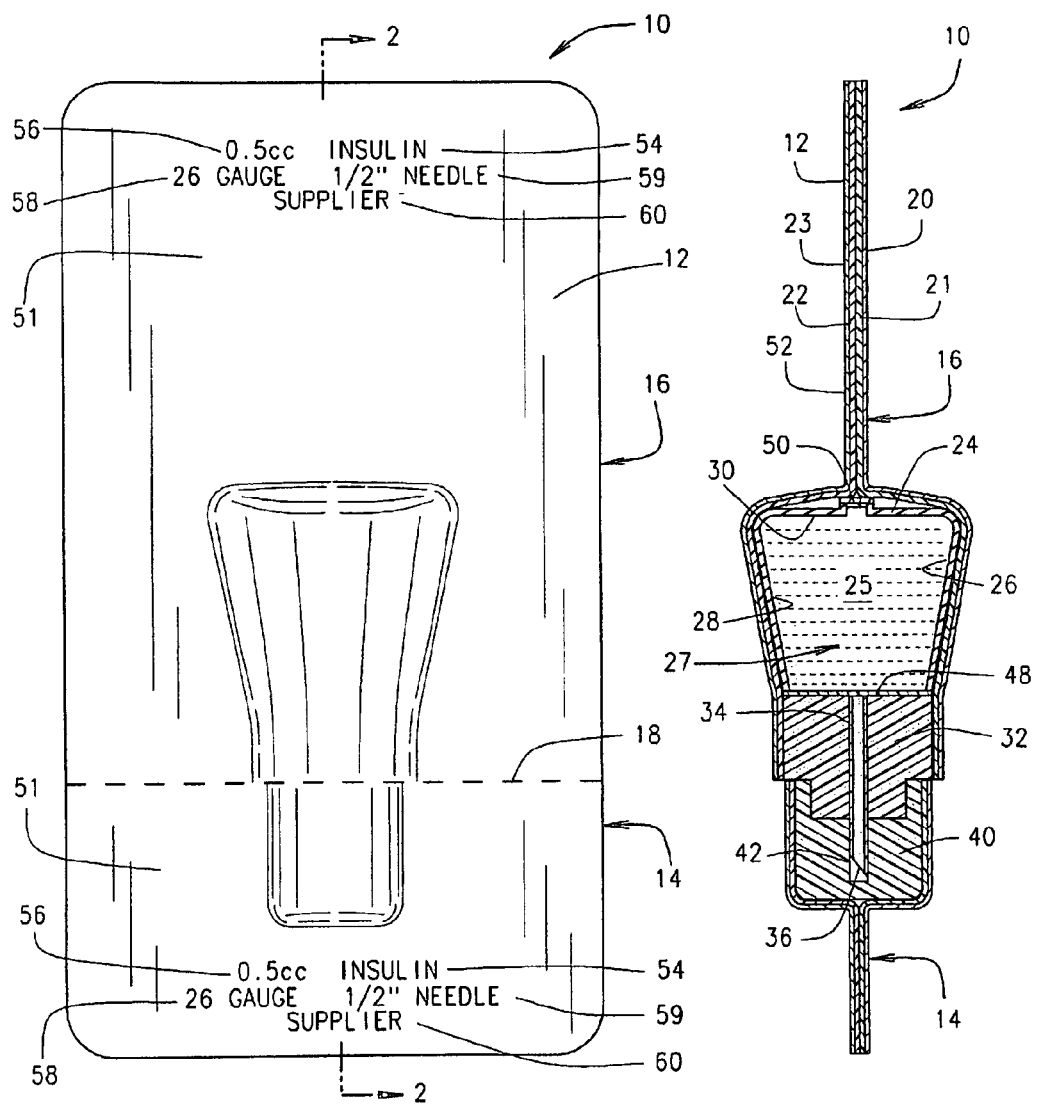
FIG. 1 is a top plan view of the unit dose disposable pharmaceutical delivery system with the tear-away portion of the envelope joined to the delivery portion.
FIG. 2 is a section view of the unit dose disposable pharmaceutical delivery system of FIG. 1 along the line 2-2.
Figure 3:
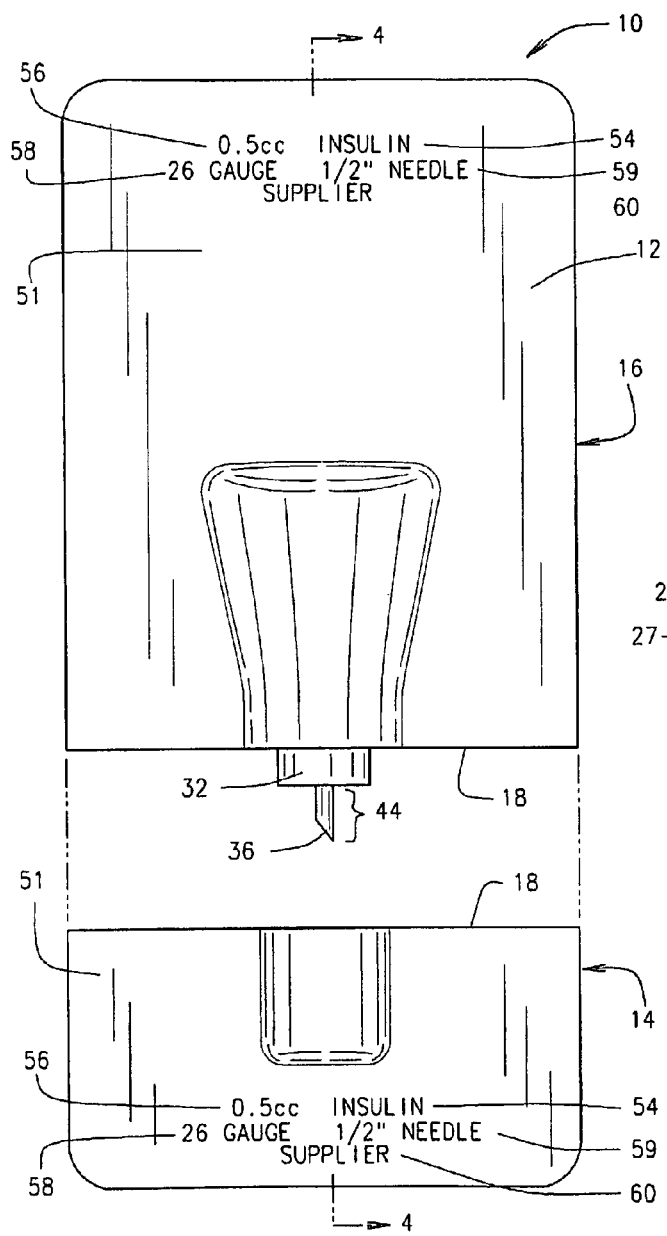
FIG. 3 is a top plan view of the unit dose disposable pharmaceutical delivery system with the tear away portion removed from the delivery portion of the envelope.
Figure 4:
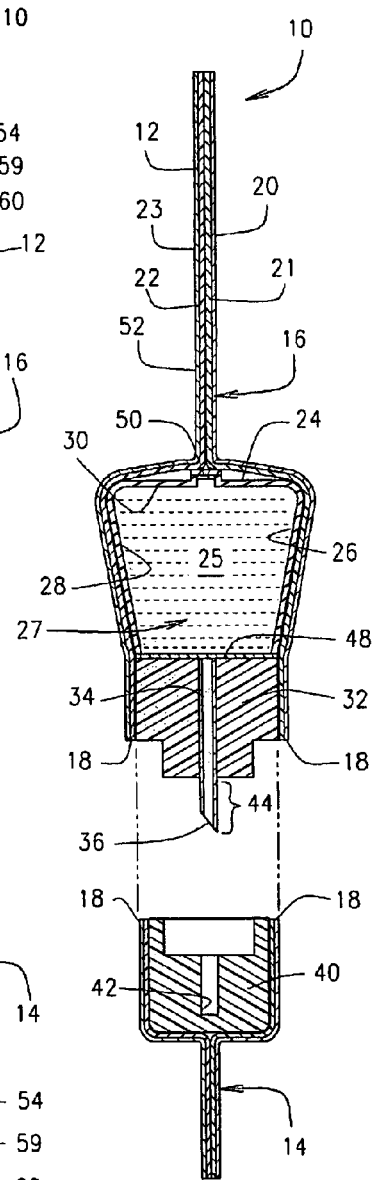
FIG. 4 is a section view of the unit dose disposable pharmaceutical delivery system of FIG. 3 along the line 4-4.

This is a description of FIGS. 1-6 of the unit dose disposable pharmaceutical delivery system generally identified by the numeral 10. The delivery system 10 forms an envelope 12 which includes the tear-away portion 14 and the dispensing portion 16. A tear line 18 divides the tear-away portion 14 from the dispensing portion 16. To separate the two portions, the user merely tears and slightly rotates the tear-away portion from the dispensing portion.

The envelope 12 may be formed from an anterior sheet 20 and a posterior sheet 22. Depending on the application, other sheets may also be used, such as second anterior sheet 21 and second posterior sheet 23. Other sheets, not shown may also be necessary. The bladder 24 may be formed separately from the sheets 20 and 22 or it may be defined by the sheets 20 and 22. FIGS. 1-6 show the bladder 24 formed separately from sheets 20, 21, 22 and 23.

In the preferred embodiment, the bladder may be formed from a relatively stiff anterior wall 26, and posterior wall 28 joined by a relatively flexible side wall 30. The bladder may be formed in different shapes depending on a variety of factors including the amount of the unit dose, the type of pharmaceutical and the intended application. The bladder may be formed from any suitable material, but polyethylene or polypropylene is preferred. The bladder 24 defines a chamber 25 to hold the pharmaceutical 27.

A rigid needle hub 32 is secured to the dispensing portion 16 of the envelope 12. A hollow needle 34 extends from the needle hub and is in a fixed position relative to the bladder. Unlike many prior art patents, the needle of the present invention does not move to puncture the bladder, prior to injection of the pharmaceutical. The needle may have a sharp point 36, a crown point 38, such as used by allergists or some other design. Any gauge needle may be used, but from about 22 gauge to about 29 gauge is preferred. A needle cap 40 is secured to the tear-away portion of the envelope and has a cavity 42 sized and arranged to receive the exposed portion of the needle 44. The exposed portion of the needle may be of any length including from about 0.25 inches to about 1.0 inches. When injecting the pharmaceutical, the bladder 24 is in fluid communication with the needle 34. However, prior to the injection, the bladder may or may not be in fluid communication with the needle as discussed below.

The delivery system may be used for any size unit dose, but preferably from about 0.5 cc to about 3.0 cc. The delivery system 10 may use the needle cap to seal the pharmaceutical in the bladder or the delivery system may have one or more seals used in addition to or in lieu of the needle cap. For example, a bladder seal 46 may be positioned between the bladder and the needle as better seen in FIGS. 5 and 6. When pressure is applied to the bladder by the thumb and forefinger, the pressurized pharmaceutical ruptures the bladder seal 46 and flows into the needle 34. The delivery system 10 may use the needle cap to seal the pharmaceutical in the bladder, as previously mentioned or the delivery system may use the bladder seal 46 and/or a needle hub seal 48, as better seen in FIGS. 5 and 6. Again, the pressurized pharmaceutical ruptures the needle hub seal 48 and/or the bladder seal 46 allowing the pharmaceutical to flow into the needle 34. Other rupture seals, not show, may also be used in this delivery system in conjunction with or in lieu of the bladder seal 46, the needle hub seal 48 and/or the needle cap 40.

A fill port 50 may be positioned in the bladder to facilitate filling of the bladder with the pharmaceutical. The fill port may be formed from a soft elastomeric compound which is easily pierced by a fill needle during the manufacturing process. In the alternative, the bladder may be filled in other ways without the need for a fill port.

The exterior surface 51 of the envelope may be printed with various types of indicia, including but not limited to, pharmaceutical indicia 54 to identify the name of the pharmaceutical in the delivery system, unit dose indicia 56 to indicate the amount of the pharmaceutical in the delivery system, needle gauge indicia 58 and needle length indicia 59. For advertising purposes, supplier indicia 60 to indicate the maker of the pharmaceutical, such as Pfizer, or the producer of the delivery system, such as Becton and Dickinson, commonly abbreviated to BD in the industry.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

What is claimed is:

1. A single dose disposable pharmaceutical delivery apparatus comprising:
    an envelope comprising a tear-away portion and a dispensing portion;
    the dispensing portion comprising:
        a bladder to contain a pharmaceutical;
        a needle;
        a needle hub; and
        one of (i) a needle hub seal or (ii) a bladder seal and a needle hub seal;
    the tear-away portion comprising a needle cap;
    wherein:
        the needle is secured to the needle hub;
        the needle cap protects an exposed portion of the needle;
        the needle is in a stationary position relative to the bladder;

the bladder seal, when present, is positioned between the bladder and the needle;
the needle hub seal is attached to the needle hub; and
the needle is fluidly connected with the bladder when (i) the needle hub seal is ruptured or (ii) the bladder seal and the needle hub seal are ruptured.

2. The apparatus of claim 1 wherein the needle cap protects an exposed sharp end portion of the needle.

3. The apparatus of claim 1 wherein the needle is fixedly attached to and extending from the needle hub.

4. The apparatus of claim 1 wherein the needle is rigidly attached to and extending from the needle hub.

5. The apparatus of claim 1 comprising indicia on an exterior of the envelope selected from the group consisting of: a name of a supplier; a unit dose; and a pharmaceutical name.

6. The apparatus of claim 1 wherein the needle cap fluidly seals the needle and removal of the tear-away portion of the envelope fluidly unseals the needle.

7. The apparatus of claim 1 comprising:
the bladder seal;
wherein
the bladder seal is positioned between the bladder and the needle;
the bladder seal is a pressure sensitive bladder seal; and
the needle is fluidly connected with the bladder upon rupture of the bladder seal.

8. The apparatus of claim 7 wherein the needle cap fluidly seals the needle and removal of the tear-away portion of the envelope fluidly unseals the needle.

9. The apparatus of claim 1 comprising:
the needle hub seal;
wherein
the needle hub seal is attached to the needle hub;
the needle hub seal is a pressure sensitive needle hub seal; and
the needle is fluidly connected with the bladder upon rupture of the needle hub seal.

10. The apparatus of claim 9 wherein the needle cap fluidly seals the needle and removal of the tear-away portion of the envelope fluidly unseals the needle.

11. The apparatus of claim 1 comprising:
the bladder seal and
the needle hub seal;
wherein:
the bladder seal is positioned between the bladder and the needle;
the bladder seal is a pressure sensitive bladder seal;
the needle hub seal is attached to the needle hub;
the needle hub seal is a pressure sensitive needle hub seal; and
the needle is fluidly connected with the bladder when the bladder seal and the needle hub seal are ruptured.

12. The apparatus of claim 11 wherein the needle cap fluidly seals the needle and removal of the tear-away portion of the envelope fluidly unseals the needle.

13. The apparatus of claim 1 comprising:
a fill port;
wherein the fill port facilitates filling of the bladder with the pharmaceutical.

14. The apparatus of claim 13 wherein the fill port is an elastomeric fill port.

15. The apparatus of claim 1 comprising the needle hub seal.

16. The apparatus of claim 1 comprising the bladder seal and the needle hub seal.

17. A single dose disposable pharmaceutical delivery apparatus comprising:
an envelope comprising a tear-away portion and a dispensing portion;
the dispensing portion comprising:
a bladder to contain a pharmaceutical;
a needle;
a needle hub;
a pressure sensitive bladder seal;
a pressure sensitive needle hub seal; and
a fill port;
the tear-away portion comprising a needle cap;
wherein:
the needle is secured to the needle hub;
the needle is in a stationary position relative to the bladder;
the needle cap protects an exposed portion of the needle;
the needle cap fluidly seals the needle and removal of the tear-away portion of the envelope fluidly unseals the needle;
the bladder seal is positioned between the bladder and the needle;
the needle hub seal is attached to the needle hub;
the needle is fluidly connected with the bladder when the bladder seal and the needle hub seal is ruptured; and
the fill port facilitates filling of the bladder with the pharmaceutical.

* * * * *